United States Patent
Osorio et al.

(10) Patent No.: US 6,486,336 B1
(45) Date of Patent: Nov. 26, 2002

(54) SUNFLOWER SEEDS AND OIL HAVING A HIGH STEARIC ACID CONTENT

(75) Inventors: Jorge Osorio, Seville; Jose Maria Fernandez, Cordoba; Manuel Mancha; Rafael Garcés, both of Seville, all of (ES)

(73) Assignee: Consejo Superior de Investigaciones Cientificas, Seville (ES)

( * ) Notice: Subject to any disclaimer, the term of this patent is extended or adjusted under 35 U.S.C. 154(b) by 1 day.

(21) Appl. No.: 09/649,288

(22) Filed: Aug. 26, 2000

Related U.S. Application Data

(63) Continuation of application No. 08/682,690, filed as application No. PCT/EP95/00369 on Jan. 31, 1995.

(30) Foreign Application Priority Data

| Jan. 31, 1994 | (ES) | 9400177 |
|---|---|---|
| Jan. 31, 1994 | (ES) | 9400178 |
| Jun. 24, 1994 | (ES) | 9401383 |
| Jun. 24, 1994 | (ES) | 9401384 |

(51) Int. Cl.$^7$ .............................................. C07C 53/00
(52) U.S. Cl. ...................... 554/224; 426/601; 426/607; 426/615
(58) Field of Search .................... 584/224; 424/601, 424/615, 607

(56) References Cited

U.S. PATENT DOCUMENTS

| 4,378,655 A | 4/1983 | Johnson |
| 4,627,192 A | 12/1986 | Fick |
| 4,627,192 A | 12/1986 | Fick |
| 743,402 | 5/1988 | Fick |

FOREIGN PATENT DOCUMENTS

| EP | 0 431 833 | 6/1991 |
| EP | 0 496 504 | 7/1992 |
| JP | 02 039834 | 2/1990 |

OTHER PUBLICATIONS

Soldatov, K.I., "High–Oleic Variety of Sunflower, Selection, Growing of Seeds and Technology of Cultivation of Technical Crops", Moscow, Kolos, 1980, pp. 35–42.

Soldatov, K.I., "Chemical Mutagenesis in Sunflower Breeding", 7th Int. Sunflower Conf., pp. 352–357.

Gerhardt N. Fick, et al., "Sunflower Breeding", Chapter 8, *Sunflower Technology and Production,* A.A. Schneiter, ed.. Agronomy Monograph No. 35. pp. 395–439 (1997).

Jerry F. Miller, et al., The Genetics of Sunflower, Chapter p, *Sunflower Technology and Production,* A.A. Schneiter, ed.. Agronomy Monograph No. 35 pp. 441–495 (1997).

Bisplinghoff, F.D., "Quality Standard for Animal and Plant Fats," Fats and Proteins Research Foundation, Inc., Fort Meyers Beach, Florida, Oct. 5, 1999.

Martínez–Force, E. et al., "Fatty Acid Composition in Developing High Saturated Sunflower (*Helianthus annus*) Seeds: Maturation Changes and Temperature Effect," Instituto de la Grasa, CSIC, Sevilla, Spain, *J. Agric. Food Chem.* 46:3577–3582, 1998.

Osorio, J. et al., "Mutant Sunflowers with High Concentration of Saturated Fatty Acids in the Oil," *Crop Sci.* 35:739–742, 1995.

Purdy, R.H., Paper Entitled "Oxidative Stability of High Oleic Sunflower and Safflower Oils," pp. 523–525, Jun. 5, 1984.

Soldatov, K.I., "Chemical Mutagenesis in Sunflower Breeding," *Sunflower Convention in Krasnubar, USSR,* 1976.

*Primary Examiner*—Deborah D. Carr
(74) *Attorney, Agent, or Firm*—Christensen O'Connor Johnson Kindness PLLC

(57) ABSTRACT

The invention relates to a sunflower seed, comprising a sunflower oil having an increased stearic acid content as compared to wild type seeds, obtainable by treating parent seeds with a mutagenic agent during a period of time and in a conceatration sufficient to induce one or more mutations in the genetic trait involved in stearic acid biosynthesis resulting in an incresed production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds. Preferably the seeds comprise an oil having a stearic acid content of between 19.1 and 35% by weight related to the total amount of fatty acids in the oil, and are obtainable by treating the parent seeds with an alkylating agent, such as ethyl methane sulfonate in water, or with sodium azide in water. The invention further relates to sunflower oil obtainable by extracting the sunflower seeds, to a method for preparing sunflower seeds having an incresed stearic acid content as compared to wild type seeds, a method for preparing a sunflower oil having an increased stearic acid content sunflower plants produced from the seeds and the use of the sunflower oil in various products.

12 Claims, No Drawings

SUNFLOWER SEEDS AND OIL HAVING A HIGH STEARIC ACID CONTENT

This application is a contention of Ser. No. 08/682,690 filed Jul. 30, 1997 which is a 371 of PCT/EP95/00369 filed Jan. 31, 1995.

The present invention relates to sunflower seeds comprising an oil having an increased stearic acid content as compared to wild type plants between 10% and 35% by weight related to the total amount of fatty acids in the oil. The invention also relates to sunflower seeds having a stearic acid content up to 54% by weight or more. The invention further relates to a sunflower oil extractable from the seeds of the invention, to sunflower plants produced from the seeds, to methods for preparing the seeds and the oil, as well as to the use of the oil in various products and to the products comprising the oil.

Sunflower is generally cultivated for obtaining oil which has saturated fatty acids (palmitic and stearic) and unsaturated fatty acids (oleic and linoleic). The stearic acid content is always less than 10% (Gustone, F. D. et al. "The lipid handbook"; Chapman and Hall 1986), normally comprised between 3% and 7%. In relation with the unsaturated fatty acids there are two different kinds of sunflower seeds: the normal sunflower which has a linoleic acid content between 50% and 70% (Knowles, P. F. "Recent advances in oil crops breeding"; AOCS Proceedings 1988) and the high oleic sunflower which has 2–10% of linoleic acid and 75–90% of oleic acid (Soldatov, K. I. "Chemical mutagenesis in sunflower breeding"; Int. Proc. 7th Intern. Sunflower Conference, 352–357, 1976). There is also a sunflower line having a high palmitic acid content, between 22% and 40% (R. Ivanov et al. "Sunflower Breeding for High Palmitic Acid Content in the Oil; Proc. of the 12th Intern. Sunflower Conference, Vol. II, 453–465, 1988) and another line with low saturated fatty acid content (6% or less) (EP-A-496504).

Table 1 shows the fatty acid composition for some known sunflower oil varieties.

TABLE 1

| | % of fatty acids in sunflower oil | | | |
|---|---|---|---|---|
| Variety | Palmitic | Stearic | Oleic | Linoleic |
| Normal[1] | 5.9 | 5.7 | 21.8 | 66.5 |
| High oleic[1] | 3.1 | 4.8 | 84.9 | 6.7 |
| Low saturated[2] | 3.9 | 2.2 | 89.9 | 4.0 |
| High palmitic[3] | 25.1 | 4.3 | 10.6 | 56.4 |

[1]Fernandez Martinez et al.; Grasas y Aceites 37, (1986)
[2]Patent EP-496504
[3]This variety has also 3.6% of palmitoleic acid The saturated fatty acid content of an oil is directly related with the physical and chemical characteristics thereof. In case that said content is sufficiently high, the oil can be a solid at room temperature like some animal fats. Normal sunflower oil is always a liquid under said conditions.

In the food industry like for the production of confectionery or margarine, animal fats or hydrogenated vegetable fats are usually used because a solid or semi-solid product is required. By means of hydrogenation unsaturated fatty acids are converted into saturated fatty acids. Animal fats as well as hydrogenated fats are not very recommendable from a nutritional point of view (chow, C. K. "Fatty acids in food and their health implications", Dekker, N.Y., 1992). Animal fats have a relatively high cholesterol content. Too much cholesterol in the diet may be detrimental to the health. Therefore animal fats have been substituted in the last years by hydrogenated vegetable fats which do not contain cholesterol.

However, said hydrogenated fats present another problem derived from the hydrogenation process. In said process positional isomerization (shift of double bonds) and stereochemical transformations (formation of "trans" isomers) take place. Isomers are produced in an amount of up to 30%–50% of the total fatty acids amount. These isomers are not very healthy from a nutritional point of view (Wood, R., "Biological effects of geometrical and positional isomers of monounsaturated fatty acids in humans"; Dekker, N.Y. (1990); Willet, W. C. & Ascherio, A., "Trans Fatty Acids: Are The Effects Only Marginal ?", American Journal of Public Health, Vol. 84, 5, (1994)). Therefore, the use of hydrogenated fats in the food industry should be avoided.

Sunflower oil has a desirable content of unsaturated fatty acids. For use in the food industry however, the stearic acid content of the oil must be higher than in the normal sunflower oil (Norris, M. E., "Oil substitutions in food formulations", Inform. 1, 388–392 (1990)) in order to obtain a more solid product.

It is thus an object of the invention to provide a new natural vegetable oil extracted from mutated seeds, the oil having a higher stearic acid content as compared to oil obtained from wild type seeds.

The invention therefore provides sunflower seeds, comprising a sunflower oil having an increased stearic acid content as compared to wild type seeds, obtainable by treating parent seeds with a mutagenic agent during a period of time and in a concentration sufficient to induce one or more mutations in the genetic trait involved in stearic acid biosynthesis resulting in an increased production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds.

Preferably the sunflower seeds according to the invention comprise an oil having a stearic acid content of between 19.1 and 35% by weight, related to the total amount of fatty acids in the oil, and are obtainable by treating the parent seeds during 2 hours at room temperature with an alkylating agent such as a solution of 70 mM ethyl methane sulfonate in water.

In another embodiment of the invention the seeds comprise an oil having a stearic acid content of between 10 and 19% by weight related to the total amount of fatty acids in the oil, and are obtainable by treating the parent seeds with a solution of 2 mM sodium azide in water during 2 hours at room temperature.

Sunflower seeds identified as "CAS-3" having an average stearic acid content of 25% by weight, related to the total amount of fatty acids in the oil, have been deposited on Dec. 14, 1994 with the American Type Culture Collection, 12301 Parklawn Drive, Rockville, Md. 20852, U.S.A. under deposit accession number ATCC 75968. Sunflower seeds identified as "CAS-4" having an average stearic acid content of 15.4% by weight, related to the total amount of fatty acids in the oil, have been deposited on the same day with the same institution under deposit accession number ATCC 75969.

Seeds having an even higher stearic acid content between 29 and 54% by weight related to the total amount of fatty acids in the oil, may be obtained according to the invention by crossing sunflowers originating from seeds having a stearic acid content between 19.1 and 35% by weight with sunflowers originating from seeds having a stearic acid content between 10 and 19% by weight, and collecting the seeds.

The invention further relates to sunflower oil having a stearic acid content of between 10 and 54% by weight, preferably between 10 and 35% by weight, related to the total amount of fatty acids in the oil, which may be obtained by extracting sunflower seeds of the invention. Sunflower oil having a stearic acid content of 15.4% by weight related to the total amount of fatty acids in the oil, may be obtained by extracting sunflower seeds having the deposit accession number ATCC 75969. Sunflower oil having a stearic acid content of 25% by weight related to the total amount of fatty acids in the oil, is obtainable by extracting sunflower seeds having the deposit accession number ATCC 75968.

Preferably the sunflower oil of the invention has a palmitic acid content between 3 and 40% by weight, an oleic acid content between 3 and 85% by weight and a linoleic acid content between 2 and 84% by weight, all related to the total amount of fatty acids in the oil. Such types of oil may be obtained from seeds produced by crossing the high stearic acid seeds of the invention with seeds having a desirable content of one or more unsaturated and/or saturated fatty acids. Thus tailor-made seeds and tailor-made oil produced therefrom may be obtained by preparing mutants according to the invention and use these in further conventional plant improvement practice by crossing them with other known or as yet unknown mutant or wild type plants.

The invention also relates to a method for preparing sunflower seeds having an increased stearic acid content as compared to wild type seeds, by treating parent seeds with a mutagenic agent during a period of time and in a concentration sufficient to induce one or more mutations in the genetic trait involved in stearic acid biosynthesis resulting in an increased production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds.

In practice the method comprises mutagenesis of sunflower seeds with a suitable mutagenic agent. The mutagenesis will produce inheritable genetic changes in the DNA of the seeds. According to the invention it was possible after several different treatments to select some treatments that produced a high number of genetic modifications in the genes that control the seed fatty acid biosynthesis. These treatments comprise the use of sodium azide or an alkylating agent, like ethyl methane sulfonate. Of course any other mutagenic agent having the same or similar effects may also be used.

Then, the next seed generation was analyzed with a new methodology described in Garcés, R. and Mancha, M. "One-step lipid extraction and fatty acid methyl esters preparation from fresh plant tissues". Analytical Biochemistry, 211:139–143, 1993. This allowed for the detection of seeds with modifications in the composition of any fatty acid. Selected seeds showing a desirably high stearic acid content have been cultivated to the fifth generation showing that this new genetic trait is inheritable and stable and independent of growth conditions.

In the method of the invention the parent seeds are for example treated during 2 hours at room temperature with a solution of 70 mM ethyl methane sulfonate in water, or during 2 hours at room temperature with a solution of 2 mM sodium azide in water.

In a further embodiment of the method of the invention, the mutation and selection steps may be followed by conventional plant improvement techniques thus leading to seeds having e.g. an even higher stearic acid content up to 54% by weight or more, or to seeds having a desirable content of one or more other fatty acids. In still another embodiment the seeds of the invention may be subjected to one or more further mutation treatments.

Sunflower oil having a stearic acid content of between 10 and 35% by weight, related to the total amount of fatty acids in the oil, may be prepared by extraction from sunflower seeds of the invention in any manner known to the person skilled in the art. Such extraction methods are well known and for example described in "Bailey's industrial oil and fat products", Vol. 2, Chapter 3; 4th Edition, John Wiley and Sons, New York (1982).

The invention further relates to sunflower plants produced from seeds according to the invention. Thus, the seeds can be used to produce parent lines that have high stearic acid content in their oil. This also applies to plants originating from seeds obtained after crossing the mutants of the invention with each other or with other seeds having a desirable phenotype. The seeds may be cultured in the normal way on soil or any other substrate. The production of the modified plants does not require any additional measure as compared to the growing of ordinary sunflower seeds.

The sunflower plants may be used in breeding programmes for the development of sunflower lines or hybrids, which programmes are aimed at the production of open pollinated or hybrid varieties meeting the requirements of farming practice regarding yield, disease resistance and other agronomically important traits in major sunflower growing areas in the world. Seeds resulting from these programmes may be used in the growing of commercial sunflower crops.

The invention also relates to the use of a sunflower oil of the invention in the food industry. The natural vegetable oil that has been extracted from mutagenized sunflowers seeds has a high stearic acid content between 10 and 35%, or in the case of intercrossing of the seeds, even up to 54% or more. This allows to use the oil from these kinds-of seeds as such. However, combinations of the oil of the invention with oil from the known high oleic acid or high palmitic acid sunflower seeds, in the production of edible fats or fat mixtures, like margarine, vegetable-dairy or in the production of confectionery or bakery is also possible depending on the requirements of the application. The advantage of these oils is that they do not have artificial fatty acid isomers, like the "trans" isomers found in the hydrogenated oils, and, of course, no cholesterol, like in the animal fats.

The invention further relates to products made by using the oil, such as margarine, vegetable-dairy, confectionery or bakery. The oil may simply replace oils or fats ordinarily used in this type of products. It is within the reach of the skilled person to determine how to use the oil without performing any inventive labor.

The present invention will be further illustrated by means of the following examples which are given for illustration purposes only and are in no way intended to limit the scope of the invention.

EXAMPLES

Materials and methods

Sodium azide and ethyl methane sulfonate were used as mutagenic agents in Example 1 and 2, respectively. Several sunflower lines with a stearic acid content between 10 and 35% have been obtained. In all these cases the original sunflower parent-line used was RDF-1-532 (Sunflower Collection of Instituto de Agricultura Sostenible, CSIC, Córdoba, Spain) that has from 4 to 7% stearic acid content in the seed oil. The preparation of the lines CAS-3 and CAS-4, and of the line CAS-3×4 obtained after crossing CAS-3 with CAS-4, have been described in the following examples.

Example 1

Seeds were mutagenized with a solution of 70 mM of ethyl methane sulfonate (EMS) in water. The treatment was performed at room temperature during 2 hours while shaking (60 rpm). After mutagenesis the EMS solution was discarded and seeds were washed during 16 hours under tap water.

Treated seeds were germinated in the field and plants were self-pollinated. The seeds collected from these plants were used to select new sunflower lines with modifications in the fatty acid composition. By using the method of Garcés, R. and Mancha, M. (supra) the seed fatty acid composition was determined by gas liquid chromatography, after converting the fatty acids into their corresponding methyl esters.

A first plant with 9 to 17% stearic acid content in the oil was selected. The progeny was cultivated for five generations wherein the stearic acid content increased and the new genetic trait became stably fixed in the genetic material of the seed. This line is called CAS-3. A selected sample of this line was analyzed resulting in a stearic acid content of 26% (Table 2). The minimum and the maximum stearic acid content of the line. were 19 and 35% respectively. The stearic acid content of oil extracted from seeds from this cell line may thus lie between 19 and 35%.

Example 2

Sunflower seeds were mutagenized with sodium azide, at a concentration of 2 mM in water. The treatment was performed at room temperature during two hours while shaking (60 rpm). Then the mutagenesis solution was discarded and seeds were washed during 16 hours with tap water.

Seeds were planted in the field and plants were self-pollinated. Seeds from these plants were collected, and the fatty acid composition was determined by gas liquid chromatography, after converting the fatty acids into their corresponding methyl esters using the method described in Example 1.

Seeds from a plant having around 10% stearic acid in the oil were selected and cultivated for five generations. During this procedure the stearic acid content was increased and the new genetic trait fixed. This line is called CAS-4. A selected sample of this line was analyzed resulting in a stearic acid content of 16.1%. The minimum and the maximum values were 12 and 19% respectively (Table 2).

TABLE 2

| | Percentage fatty acids | | | |
|---|---|---|---|---|
| Line | Palmitic | Stearic | Oleic | Linoleic |
| RDF-1-532 | 6.7 | 4.5 | 37.4 | 51.3 |
| CAS-3 | 5.1 | 26.0 | 13.8 | 55.1 |
| CAS-4 | 5.5 | 16.1 | 24.3 | 54.1 |

Example 3

Sunflower plants were grown from the sunflower seeds CAS-3 and CAS-4. The plants thus obtained were artificially pollinated in order to ensure only crossings between CAS-3 and CAS-4 to occur, not pollination of the mutant plants amongst themselves.

From the seeds thus produced plants were grown and the stearic acid content of the progeny was determined as described in Examples 1 and 2. The hybrid CAS-3×4 had a stearic acid content of more than 35% by weight. From this it appears that intercrossing the mutants will yield hybrids with an even higher stearic acid content.

According to the invention sunflower plants and seeds from which said oil can be extracted have been obtained by means of a biotechnological process. This high stearic acid content is an inheritable trait and is independent from the growing conditions.

What is claimed is:
1. Sunflower oil having a stearic acid content between 1 and 54% by weight related to the total amount of fatty acids in the oil.
2. Sunflower oil as claimed in claim 1, characterized in that the oil has a stearic acid content of 10 to 19% by weight related to the total accent of fatty acids in the oil.
3. Sunflower oil as claimed in claim 1 or 2, characterized in that the oil has a stearic acid content of 15.4% by weight related to the total amount of fatty acids in the oil.
4. Sunflower oil as claimed in claim 1, characterised in that the oil has a stearic acid content between 19.1 and 35% by weight elated to the total amount of fatty acids in the oil.
5. Sunflower oil as claimed in claim 1 or 4, characterized in that the oil has a stearic acid content of 25% by weight related to the total amount of fatty acids in the oil.
6. Sunflower oil as claimed in claim 1, characterized in that the oil has a stearic acid content between 29 and 54% by weight related to the total amount of fatty acids in the oil.
7. Sunflower oil as claimed in any one of the claims 1–6, further having a palmitic acid content between 3 and 40% by weight, an oleic acid content between 3 and 85% by weight and a linoleic acid content between 2 and 84% by weight, all related to the total amount of fatty acids in the oil.
8. Sunflower oil as claimed in claims 1–7, further comprising an oil having a high oleic acid content.
9. Sunflower oil as claimed in claims 1–7, further comprising an oil having a high palmitic acid content.
10. Sunflower oil as claimed in claims 1–7, further comprising an edible fat.
11. Sunflower oil as claimed in claims 1–7, wherein the sunflower oil is incorporated into a food product.
12. Sunflower oil as claimed in claim 11, wherein the food product is at least one of a margarine, a vegetable-dairy, a confectionery product, and a bakery product.

* * * * *

UNITED STATES PATENT AND TRADEMARK OFFICE
CERTIFICATE OF CORRECTION

PATENT NO. : 6,486,336 B1
DATED : November 26, 2002
INVENTOR(S) : J. Osorio et al.

It is certified that error appears in the above-identified patent and that said Letters Patent is hereby corrected as shown below:

Title page,
Item [56], References Cited, U.S. PATENT DOCUMENTS, delete the second occurrence of "4,627,192 A 12/1986 Fick"
OTHER PUBLICATIONS, "Meyers" should read -- Myers --; and "*annus*)" should read -- *annuus*) --

Column 1,
Line 4, "contention" should read -- continuation --
Line 34, "in the Oil;" should read -- in the Oil"; --
Line 49, "[1]Fernandez Martinez" should read -- [1]Fernández Martínez --
Line 64, "(chow," should read -- (Chow, --

Column 4,
Line 39, "kinds-of" should read -- kinds of --

Column 5,
Lines 2-3, "C
            órdoba," should not break
Line 29, "line. were" should read -- line were --

Column 6,
Line 24, "between 1" should read -- between 10 --
Line 36, "elated" should read -- related --

Signed and Sealed this

Tenth Day of June, 2003

JAMES E. ROGAN
*Director of the United States Patent and Trademark Office*